US009585715B2

(12) United States Patent
Strobl

(10) Patent No.: US 9,585,715 B2
(45) Date of Patent: Mar. 7, 2017

(54) ELECTROSURGICAL SEALING AND TRANSECTING DEVICES AND METHODS WITH IMPROVED APPLICATION OF COMPRESSIVE FORCE

(71) Applicant: Ethicon Endo-Surgery, LLC, Guaynabo, PR (US)

(72) Inventor: Geoffrey S. Strobl, Williamsburg, OH (US)

(73) Assignee: Ethicon Endo-Surgery, LLC, Guaynabo, PR (US)

(*) Notice: Subject to any disclaimer, the term of this patent is extended or adjusted under 35 U.S.C. 154(b) by 325 days.

(21) Appl. No.: 14/149,279

(22) Filed: Jan. 7, 2014

(65) Prior Publication Data
US 2015/0190191 A1 Jul. 9, 2015

(51) Int. Cl.
A61B 18/18 (2006.01)
A61B 18/14 (2006.01)
A61B 18/00 (2006.01)

(52) U.S. Cl.
CPC .. A61B 18/1445 (2013.01); A61B 2018/0063 (2013.01); A61B 2018/1455 (2013.01)

(58) Field of Classification Search
CPC .... A61B 2017/2933; A61B 2017/2934; A61B 2017/2936; A61B 17/295; A61B 18/1447; A61B 2018/1452; A61B 2018/1455
See application file for complete search history.

(56) References Cited

U.S. PATENT DOCUMENTS

| 5,350,355 A * | 9/1994 | Sklar | A61B 17/320016 604/23 |
| 6,500,176 B1 * | 12/2002 | Truckai | A61B 18/1445 606/205 |
| 6,773,409 B2 * | 8/2004 | Truckai | A61B 17/320092 601/2 |
| 8,496,682 B2 * | 7/2013 | Guerra | A61B 17/295 606/205 |
| 8,696,665 B2 * | 4/2014 | Hunt | A61B 17/295 606/205 |
| 8,939,972 B2 * | 1/2015 | Twomey | A61B 18/1445 606/51 |
| 9,119,657 B2 * | 9/2015 | Shelton, IV | A61B 17/29 |
| 9,144,456 B2 * | 9/2015 | Rosa | A61B 18/1445 |
| 9,149,325 B2 * | 10/2015 | Worrell et al. | A61B 18/1445 |
| 9,179,911 B2 * | 11/2015 | Morgan | A61B 17/0644 |

* cited by examiner

Primary Examiner — Ronald Hupczey, Jr.
(74) Attorney, Agent, or Firm — Nutter McClennen & Fish LLP

(57) ABSTRACT

Devices and methods for sealing and cutting tissue are provided. In one exemplary embodiment, a surgical device includes a pair of opposed, pivoting jaws, a cutting blade assembly slidably coupled to the jaws, and a biasing member disposed in a portion of the cutting blade assembly and configured to be received by a track formed between proximal ends of the jaws. The cutting blade assembly can be operative to open and close the jaws, and the biasing member can be configured to be disposed at a location in the track that applies a spring bias to a proximal end of at least one of the jaws. The spring bias in turn increases a compressive force applied by distal ends of the jaws, which in turn can maintain or increase a force applied to tissue disposed between the jaws. Other devices and methods for sealing and cutting tissue are also provided.

39 Claims, 9 Drawing Sheets

ELECTROSURGICAL SEALING AND TRANSECTING DEVICES AND METHODS WITH IMPROVED APPLICATION OF COMPRESSIVE FORCE

FIELD

The present invention relates to electrosurgical devices and methods for sealing and transecting tissue, and more particularly to improved devices and methods for applying compression to tissue disposed in a working end of such devices.

BACKGROUND

Surgical devices are used in various open, endoscopic, and laparoscopic surgeries to seal and transect tissue volumes and blood vessels. The devices generally include jaws for grasping tissue therebetween and a cutting mechanism that is advanced through the grasped tissue to transect it. In some instances the devices are configured to apply electrical energy to the grasped tissue to seal it before tissue transection is completed. For example, various mono-polar and bi-polar radio frequency (RF) surgical instruments and surgical techniques have been developed for sealing tissue volumes and blood vessels. Electrodes can be disposed on a face of one or both of the jaws and can apply energy to the grasped tissue to promote hemostasis.

One issue that can plague electrosurgical devices of the nature described above is the amount of compression supplied to tissue volumes or blood vessels by the jaws prior to transection. While RF energy is being delivered to tissue grasped by the jaws, the amount of compression supplied by the jaws to the grasped tissue can actually decrease. This can occur because the grasped tissue can become thinner as the energy is applied to it. Generally, the thicker the tissue or vessel, the more pronounced the decrease in compression can be. An insufficient amount of compression supplied by the jaws to the tissue can cause the tissue to undesirably slip. In an effort to counteract this tendency, devices may be designed with very tight tolerances to try and reduce the likelihood of slippage. Such efforts are not always successful, however, and furthermore reliance on tight tolerances can negatively impact the manufacturing process. Additionally, some efforts to maintain or supply additional compressive force to the jaws of some electrosurgical devices can result in undesirable initial loads being applied to the cutting mechanism. High levels of load placed on the cutting mechanism prior to transection can negatively impact the performance of the cutting mechanism.

Accordingly, there remains a need for improved surgical devices that maintain and/or increase the amount of compressive force supplied by its jaws to tissue grabbed therebetween without applying unnecessary loads to the cutting mechanism of such devices.

SUMMARY

Devices and methods are generally provided for sealing and cutting volumes of tissue and blood vessels. In one exemplary embodiment, a surgical device includes a jaw assembly, a cutting blade assembly, and a biasing member. The jaw assembly can have a first jaw and a second jaw pivotally coupled thereto, with the first and second jaws being configured to engage tissue therebetween. The cutting blade assembly can be slidably coupled to the first and second jaws. As a result, distal advancement of the cutting blade assembly along the first and second jaws can move the second jaw toward the first jaw into a closed position, and proximal retraction of the cutting blade assembly along the first and second jaws can allow the second jaw to pivot away from the first jaw into an open position. The biasing member can be coupled to the cutting blade assembly. Further, the biasing member can be configured to apply a compressive force to the second jaw during initial distal advancement of the cutting blade assembly along a proximal portion of the first and second jaws. The biasing member can also be configured to apply no compressive force to the second jaw during further distal advancement of the cutting blade assembly along a distal portion of the first and second jaws.

The second jaw can be pivotally coupled to the first jaw at a pivot point. The pivot point can be located, for example, distal of the proximal portion of the first and second jaws along which the first compressive force is applied. In some embodiments, the biasing member can be configured to travel along a first path during distal advancement of the cutting blade assembly, and travel along a second alternate path during proximal retraction of the cutting blade assembly. A leaf spring can be coupled to the first jaw and configured to bias the biasing member into the second alternate path during proximal retraction of the cutting blade assembly.

The biasing member can include a pin that is configured to abut a proximal end of the second jaw to bias the second jaw toward the closed position during initial distal advancement of the cutting blade assembly. The pin can be receiving within a track formed between the first and second jaws. In embodiments that include a leaf spring coupled to the first jaw, the leaf spring can be configured to bias the pin away from the proximal end of the second jaw during further distal advancement of the cutting blade assembly along a distal portion of the first and second jaws.

The cutting blade assembly can include a pusher shaft having a slot formed therein. The biasing member, e.g., the pin, can be slidably disposed within the slot. The slot can include a first portion that extends in a proximal-distal direction, and a second portion that extends substantially perpendicular to the first portion. In some embodiments, an electrode can be coupled to at least one of the first and second jaws and can be configured to apply energy to tissue disposed between the first and second jaws.

In another exemplary embodiment of a surgical device, the device includes an elongate shaft having an end effector with opposed jaws on a distal end thereof and an actuation assembly coupled to the opposed jaws. The actuation assembly can be configured to advance distally along the opposed jaws to close the jaws, and to retract proximally along the jaws to allow the jaws to open. Further, the actuation assembly can include a pin coupled thereto and configured to travel along a first pin path during distal advancement of the actuation assembly, and along a second alternative pin path during proximal retraction of the actuation assembly. The pin can apply an increased compressive force to the opposed jaws during at least a portion of travel along the first pin path. Further, the pin can apply no compressive force to the opposed jaws during travel along the second alternative pin path.

In some embodiments, a spring can be provided as part of the device. The spring can bias the pin into the second alternative path during proximal retraction of the actuation assembly. The actuation assembly can include a cutting blade that is configured to cut tissue engaged between the opposed jaws. The jaws can include a cartridge assembly and an anvil, which can be pivotally coupled to one another at a pivot point. In such embodiments, the pin can be configured to apply the increased compressive force to the opposed jaws during a portion of travel along the first pin path that is located proximal to the pivot point.

One exemplary method for sealing tissue includes distally advancing a cutting assembly of a surgical access device to apply a first compressive force to at least one of a first jaw and a second jaw of the device to move the jaws into a closed position in which the tissue is clamped by the jaws. The device can include a biasing element coupled to the cutting assembly that applies a second compressive force to the second jaw when the jaws are in the closed position. The method can also include further distally advancing the cutting assembly along the first and second jaws such that the biasing element no longer applies the second compressive force to the second jaw.

In some embodiments, the method can also include delivering energy to the tissue through at least one of the first and second jaws. The application of energy can occur prior to the step of further distally advancing the cutting assembly along the first and second jaws such that the biasing element no longer applies the second compressive force to the second jaw. The biasing member can travel along a path formed between the first and second jaws. Further, the biasing member can apply the second compressive force to a proximal end of the second jaw. In some embodiments, the method can also include proximally retracting the cutting assembly, with the biasing member traveling along an alternate path during proximal movement such that the biasing member applies no compressive force to the second jaw. When the cutting assembly is being further distally advanced along the first and second jaws, the tissue disposed between the jaws can be transected by the cutting assembly.

BRIEF DESCRIPTION OF DRAWINGS

This invention will be more fully understood from the following detailed description taken in conjunction with the accompanying drawings, in which.

DETAILED DESCRIPTION

Figure 1:
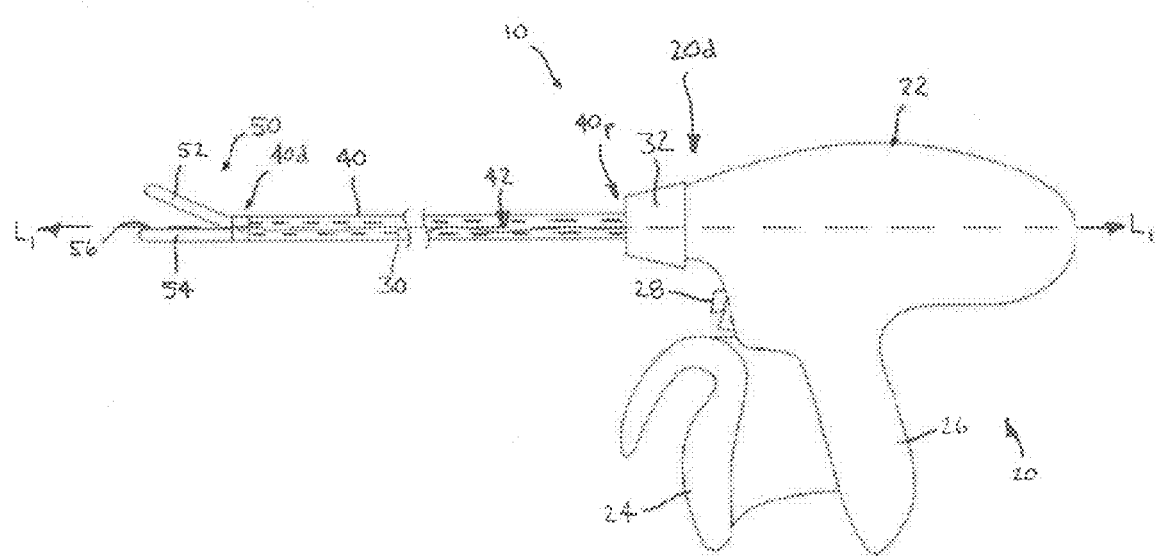
FIG. 1 is a side view of one exemplary embodiment of a surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute. Further, a person skilled in the art will recognize that a number of different terms can be used interchangeably while still being understood by the skilled person. By way of non-limiting example, the terms "cut" and "transect" are generally used interchangeably herein.

The present disclosure generally relates to surgical devices and methods for sealing and transecting tissue or blood vessels, collectively referred to herein as "tissue." The devices disclosed or otherwise derivable from the disclosures herein include features that supply a spring bias to maintain and/or increase an amount of force applied to tissue grasped by jaws of the device. In one exemplary embodiment, the application of the spring bias occurs after the jaws are closed, during the time tissue is being sealed, but before the tissue is fully transected. As described herein, the spring bias-supplying features, referred to herein as a biasing member or biasing element, can include a cantilever beam or pin configured to engage proximal ends of the jaws such that the beam acts like a spring, biasing at least one of the proximal ends of the jaws away from the other. The force supplied by the biasing member to the proximal end of the jaw results in a distal end of that jaw being biased towards the distal end of the other jaw. As a result, a compressive force applied by the jaws to tissue disposed therebetween can be maintained and/or increased. The biasing member can further be configured to slide out of a location at which it provides the spring bias after the spring bias is no longer desired, for example during a final transecting or cutting stroke. More particularly, the biasing member can be configured to travel along a path or track formed in and/or by the proximal ends of the jaws that allows the biasing member to be selectively moved between a location at which it supplies the spring bias and locations at which it does not supply the spring bias, as described in greater detail below.

FIG. 1 illustrates one embodiment of a surgical access device 10 configured to grasp, seal, and transect tissue. The surgical device can include a proximal handle portion 20, a shaft 40, and an end effector 50 for grasping tissue. The handle portion 20 can be designed to operate various features of the end effector 50. For example, the handle portion can close and open a jaw assembly of the end effector 50 to grasp tissue. The jaw assembly can include jaws 52, 54 that are configured to pivot with respect to each other to grasp tissue disposed therebetween. By way of further non-limiting example, the handle portion 20 can initiate the supply of electrical energy to one or more electrodes 56 associated with either or both of the jaws 52, 54 to weld or otherwise seal portions of the grasped tissue. The components to initiate these actions can be part of the handle portion 20 and can extend through or be electrically or mechanically coupled to components that extend through the shaft 40. Components of this nature are known to those skilled in the art, and thus further elaboration related to the same is unnecessary. Further, the handle portion 20 can also be configured to operate other components that work in conjunction with the end effector 50, such as a cutting blade assembly 80 (FIGS. 2, 5A, and 5B) that extends through the shaft 40 and is configured to cut tissue grasped by the jaws 52, 54. In some embodiments the cutting blade assembly 80 can also serve as a compression member by being configured to move the jaws 52, 54 from an open to a closed position, as described in further detail below.

The handle portion 20 can have any type of design known in the art for operating end effectors 50. In the illustrated embodiment, the handle portion 20 has a pistol-grip configuration that includes a housing 22, an actuating handle 24, and a stationary handle 26. Movement of the actuating handle 24 towards the stationary handle 26 can be effective to perform a variety of functions. In the illustrated embodiment, the actuating handle 24 is effective to advance the cutting blade assembly 80 distally to both close the jaws 52, 54 and cut tissue disposed between the jaws. In some embodiments, the actuating handle 24 can move through two separate cycles or strokes to perform these functions. For example, the actuating handle 24 can move through a first cycle or stroke in which it first moves towards the stationary handle 26 and then returns back to its initial position, during which time its movement towards the stationary handle 26 is effective to close the jaws 52, 54. The actuating handle 24 can then move through a second cycle or stroke, again moving towards the stationary handle 26 and then returning back to its initial position, during which times its movement towards the stationary handle 26 is effective to pass the cutting blade assembly 80 through at least a portion of the jaws 52, 54 to cut tissue disposed therebetween. As the actuating handle 24 returns to the initial position during the second stroke, the cutting blade assembly 80 can retract proximally with respect to the jaws 52, 54. In some embodiments, during the second return stroke the cutting blade assembly 80 can retract to its initial position so that the jaws 52, 54 open, while in other embodiments, a separate actuation can be performed to fully retract the cutting blade assembly 80 to its initial position to open the jaws 52, 54.

The mechanical and electrical components associating the actuating handle 24 with the jaws 52, 54 and or the cutting blade assembly 80 can be disposed in the housing 22 and the shaft 40, including motors, controllers, and levers, among other components. Other designs that can be used to actuate the jaws 52, 54 and the cutting blade assembly 80 include but are not limited to actuator levers, triggers, and sliders. Further, a person skilled in the art will recognize other functions that the actuating handle 24, or other means of actuation, can perform without departing from the spirit of the present disclosure.

The illustrated embodiment also includes an actuator, e.g. a button 28, as part of the handle portion 20. The button 28 can be configured such that pressing it completes a circuit to power the electrode(s) 56 to seal tissue disposed in the jaws 52, 54. More particularly, completion of the circuit by the button 28 allows electrical energy to pass from a power source disposed in the housing 22, through one or more electrical leads 30, and to the electrode 56. The electrical lead can be disposed in the shaft 40 to electrically connect the button 28 and the electrode 56. Although the power source is described as being in the housing 22, in other embodiments the power source can be external of the housing 22 and the housing can be configured to electrically connect to the power source, for instance by way of a socket extending from the housing 22 to connect to the power source. Similar to the actuating handle 24, a person skilled in the art will recognize that the actuator can have a variety of other designs, and can perform a variety of other types of functions, without departing from the spirit of the present disclosure.

Other features to assist in moving and actuating the components of the device 10 can also be incorporated into the handle portion 20. By way of example, the handle portion 20 can include a rotatable knob 32 disposed at a distal end 20d of the handle portion 20 to facilitate rotation of the shaft 40, and thus the end effector 50 coupled thereto, with respect to the handle portion 20 around a centrally disposed longitudinal axis $L_1$ of the shaft 40. A person skilled in the art will recognize other non-limiting examples of features that can be incorporated with the handle portion 20 to assist in manipulating or otherwise operating the device include: (1) an articulation lever for articulating the end effector 50; (2) a retraction handle for retracting the cutting blade assembly 80 towards and/or to its initial position in place of or independent of any retraction that is part of a firing stroke initiated by the actuating handle 24; (3) a firing lockout assembly to prevent the cutting blade assembly 80 from being actuated at an undesirable time; and (4) an emergency return button to retract the cutting blade assembly 80 before a firing stroke is completed, for instance in a case where completing the firing stroke may cause tissue to be undesirably cut. Although features such as an articulation lever, a retraction handle, a firing lockout assembly, and an emergency return button are not explicitly illustrated in the device 10, a person skilled in the art will recognize a variety of configurations for each feature that can be incorporated into the handle portion 20 and/or other portions of the device 10 without departing from the spirit of the present disclosure.

The shaft 40 can be removably coupled to the distal end 20*d* of the handle portion 20 at a proximal end 40*p* of the shaft 40 and can include a bore 42 extending therethrough for passing mechanisms to help actuate the jaws 52, 54, or to perform other functions at the surgical site, such as cutting or delivering electrical energy for sealing. In the described embodiment, the cutting blade assembly 80 (not shown) and leads 30 are coupled to the components of the handle portion and extend through the shaft 40 to the end effector 50. A distal end 40*d* of the shaft 40 can be configured to receive the end effector 50 by any known means for coupling an end effector to a shaft, including by a removable connection that allows various end effectors to be removably and replaceably coupled to the distal end 40*d*. While the shaft 40 can have any number of shapes and configurations, depending, at least in part, on the configurations of the other device components with which it is used and the type of procedure in which the device is used, in the illustrated embodiment the shaft 40 is generally cylindrical and elongate.

Figure 2:
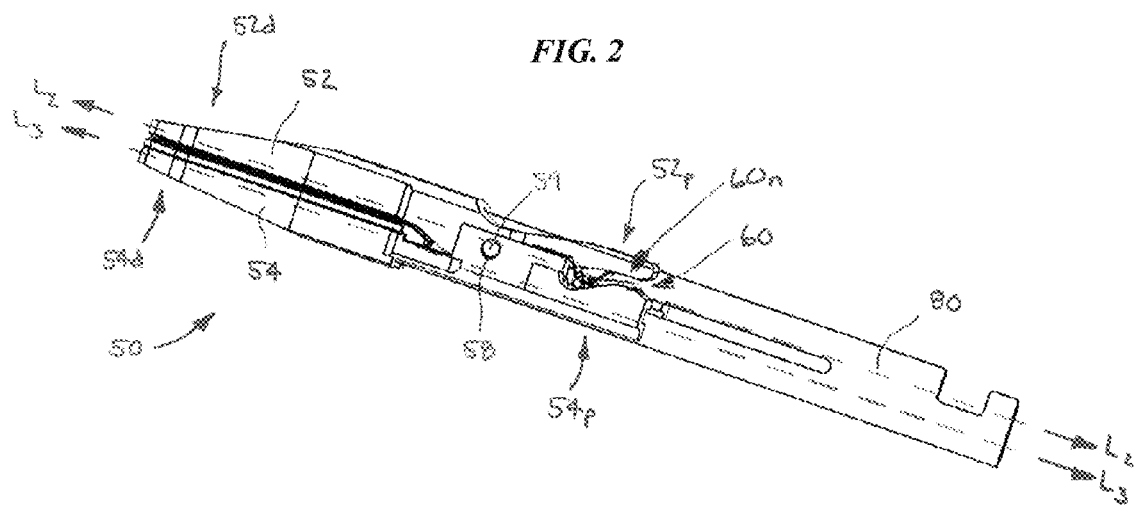
FIG. 2 is a perspective view of an end effector and cutting blade assembly of the surgical device of FIG. 1, the end effector having upper and lower jaws in a closed position.

The end effector 50 can have a variety of sizes, shapes, and configurations. As shown in FIG. 2, the end effector 50 is a clamp having upper and lower jaws 52, 54 that are pivotally connected to each other so they can rotate with respect to each other to grasp tissue therebetween. A pivot point 58 at which the jaws 52, 54 are pivotally connected by way of a pivot pin 59 can be located distal of proximal ends 52*p*, 54*p* of the jaws so that the proximal ends 52*p*, 54*p* can form a track or path 60 for receiving the cantilever beam or pin 70 (FIGS. 6 and 7) that provides the spring bias to the jaws 52, 54 when the jaws are disposed in a closed, clamped position, as discussed in detail below. When the jaws 52, 54 are in the closed position, a longitudinal axis $L_2$ extending through a length of the upper jaw 52 can be substantially parallel to a longitudinal axis $L_3$ extending through a length of the lower jaw 54 and the jaws 52, 54 can be in direct contact.

Figure 3A:
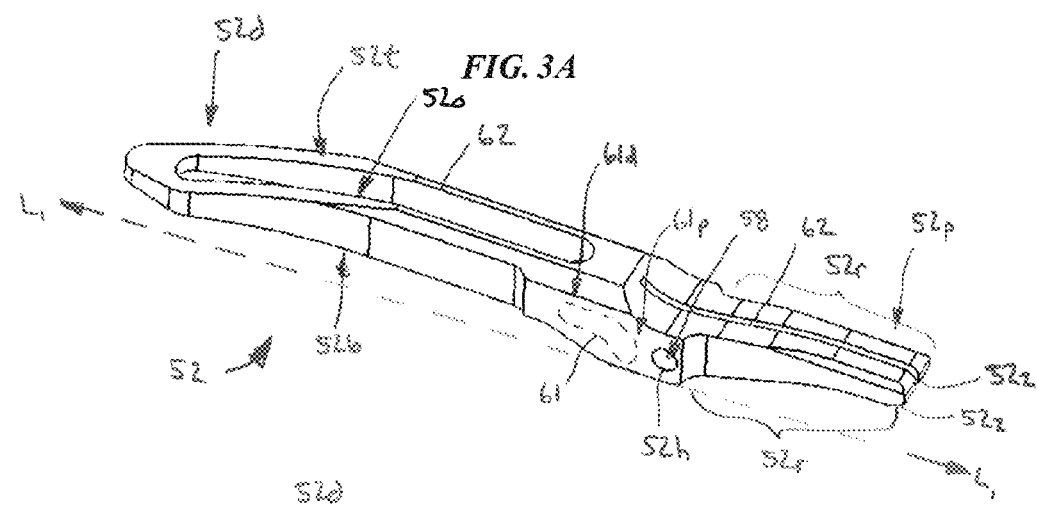
FIG. 3A is a top perspective view of the upper jaw of FIG. 2.
Figure 3B:
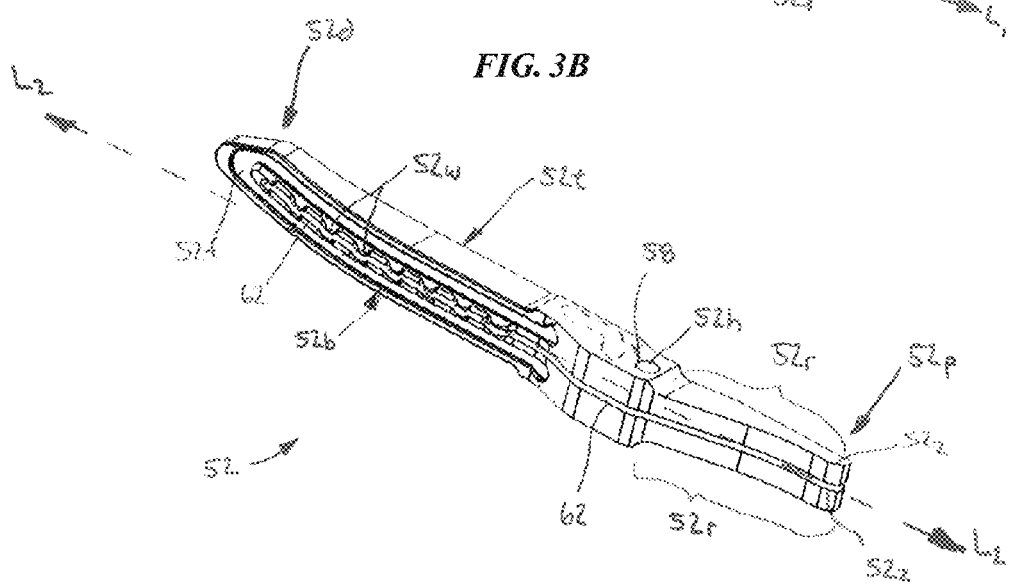
FIG. 3B is a bottom perspective view of the upper jaw of FIG. 3A.
Figure 8A:
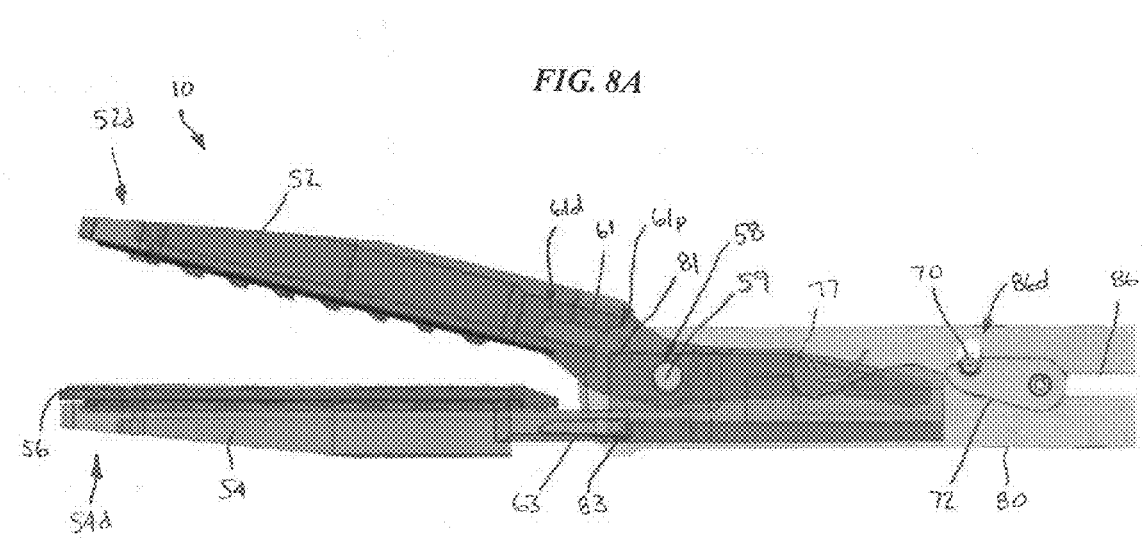
FIG. 8A is a partially transparent side view of the upper and lower jaws of FIG. 6 in an open position.

The upper jaw 52, illustrated in FIGS. 3A and 3B and alternately referred to as a second jaw or anvil, can be generally elongate in shape, having a bottom surface 52*b* that is configured to grasp tissue. The upper jaw 52 can also be configured to operate as an anvil to deploy staples of a staple cartridge associated with the lower jaw 54. As shown, a first portion 52*f* of the bottom surface 52*b* is substantially flat and complementary to a substantially flat surface located on a top surface 54*t* of the bottom jaw 54 (FIGS. 4A and 4B), and a second portion 52*w* includes teeth that can grip the tissue by increasing the friction therebetween. Opposed first slots 61 (only one is illustrated) can be formed in an internal portion of the body of the upper jaw 52 to receive a portion of the cutting blade assembly 80, e.g., a first guide 81 (FIG. 8A). As described herein, the first guide 81 can translate through the first slots 61 to apply a compressive force to the upper jaw 52. As shown, the slots 61 can have a ramped or sloped profile such that a proximal end 61*p* of the slot 61 is disposed closer to the longitudinal axis $L_1$ than the distal end 61*d* is, thus allowing a compressive force supplied by the cutting blade assembly 80 to be increased when the cutting mechanism advances distally. The increase in the compressive force can result in the distal end 52*d* of the upper jaw 52 advancing toward the distal end 54*d* of the lower jaw 54.

A second slot 62 can be formed in the upper jaw 52 for receiving a vertically extending body portion of the cutting blade assembly 80. As shown in FIG. 3B, the slot 62 extends through a substantial portion of the bottom surface 52*b*. In the top surface 52*t*, the slot 62 extends from the proximal end 52*p* to a location distal of opposed bores 52*h* (only one is illustrated) at which the pivot point 58 is located. The slot 62 then terminates before starting again in the form of a larger opening 52*o*. The portions of the slot 62 formed in the top surface 52*t*, including the opening 52*o*, and the portions of the slot 62 formed in the bottom surface 52*b* extend through the entire vertical height of the body of the upper jaw 52, thereby creating an opening that extends from the bottom surface 52*b* and through to the top surface 52*t*.

Figure 4A:
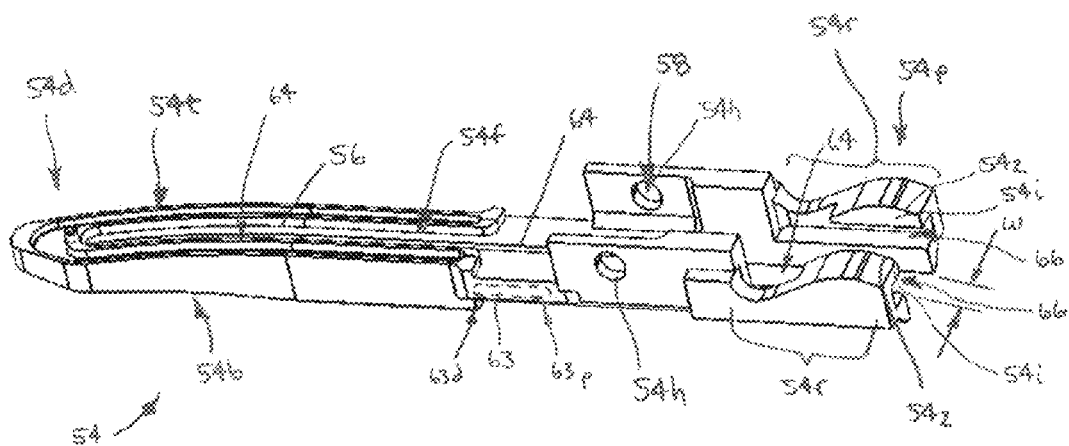
FIG. 4A is a top perspective view of the lower jaw of FIG. 2.
Figure 4B:
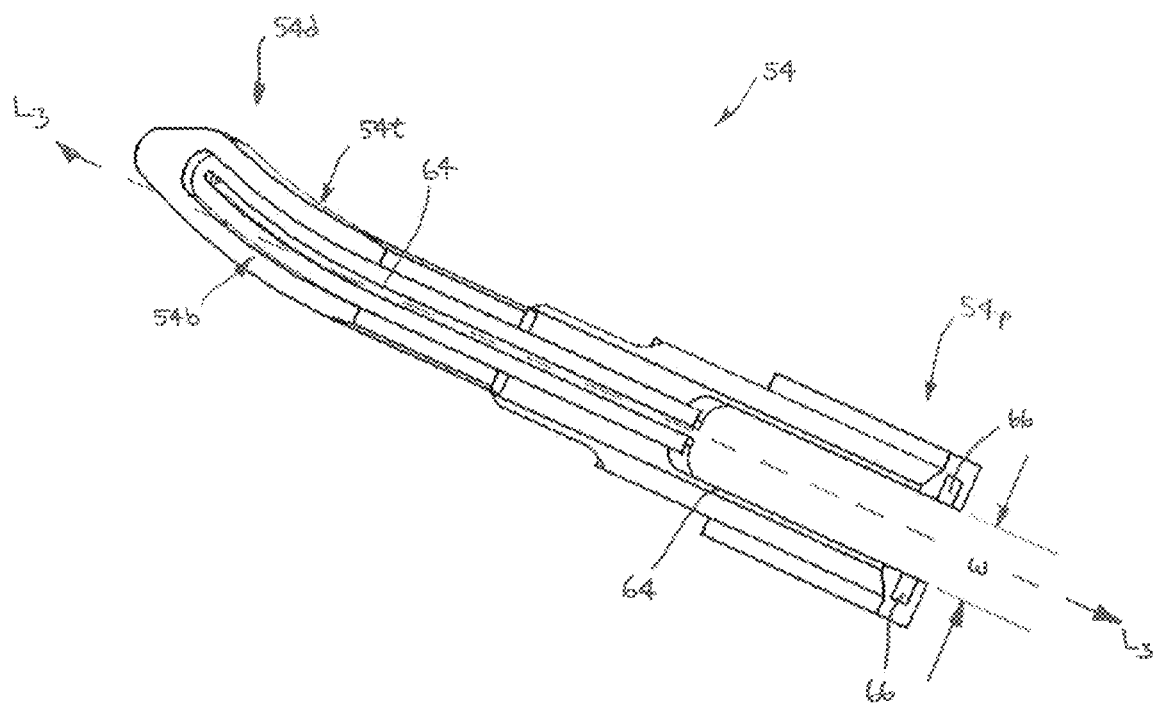
FIG. 4B is a bottom perspective view of the lower jaw of FIG. 4A.

The lower jaw 54, illustrated in FIGS. 4A and 4B and alternately referred to as a first jaw, can also be generally elongate in shape, having a top surface 54*t* that is configured to grasp tissue. The lower jaw 54 can also be configured to operate as a cartridge assembly to supply staples to tissue grasped by the jaws 52, 54. For example, the lower assembly 54 can include one or more channels (not shown) formed therein for receiving a staple cartridge, from which staples can be ejected into the tissue. As shown, a first portion 54*f* of the top surface 54*t* has the electrode 56 disposed thereon, and the electrode 56 is substantially flat and complementary to the substantially flat surface of the first portion 52*f* of the upper jaw 52. Opposed first slots 63 (only one is illustrated) can be formed in an internal portion of the body of the lower jaw 51 to receive a portion of the cutting blade assembly 80, e.g., a second guide 83 (FIG. 8A). As described herein, the second guide 83 can translate through the second slots 63. As shown, the slots 63 can maintain a substantially straight profile from its proximal end 63*p* to its distal end 63*d*.

Figure 6:
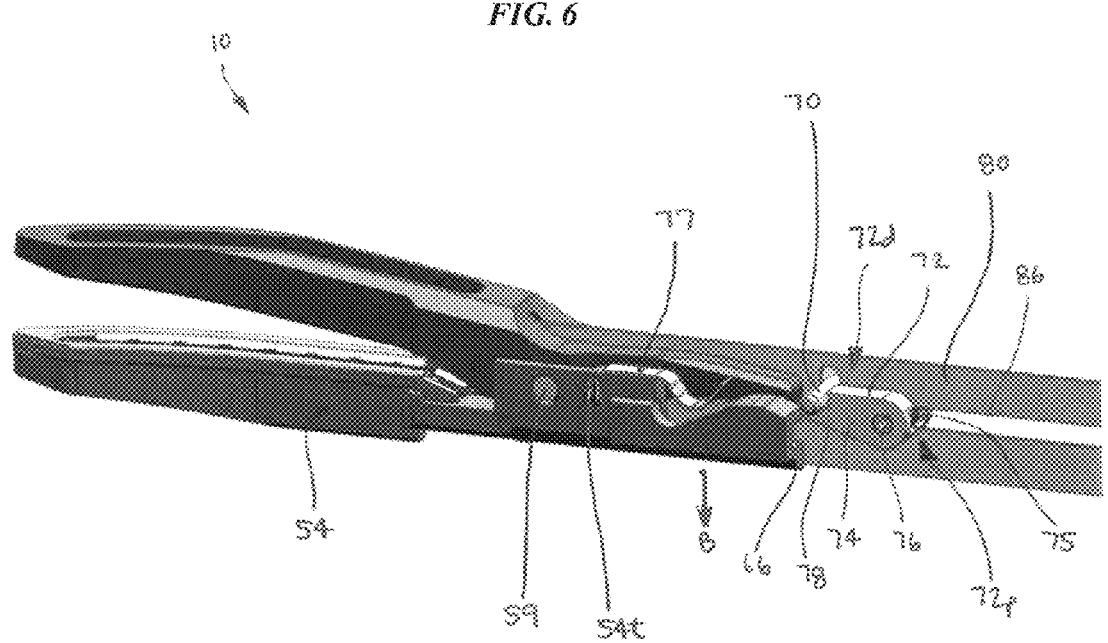
FIG. 6 is a perspective view of the upper and lower jaws of FIG. 2 in an open position.

A second slot 64 can be formed in the lower jaw 54 for receiving the vertically extending body portion of the cutting blade assembly 80. As shown in FIGS. 4A and 4B, the slot 64 extends between the top and bottom surfaces 54*t*, 54*b* throughout a substantial portion of the length of the lower jaw 54. A width w of the slot 64 at a proximal end 54*p* of the lower jaw 54 is substantially larger than a width at a more distal location so that the slot 64 can receive the proximal end 52*p* of the upper jaw 52 when the jaws 52, 54 are in an open position (FIGS. 6 and 8A). Opposed bores 54*h* can be formed in the lower jaw 54 at the pivot point 58 so that a pivot pin 59 (FIGS. 2 and 6) can be received by the bores 52*h* and the bores 54*h* to form the pivot point 58.

The electrode 56 can be coupled to the top surface 54*t* of the lower jaw using any manner known to those skilled in the art, including, by way of non-limiting example, using an adhesive. In some exemplary embodiments, the electrode can made from a positive temperature coefficient (PTC) polymer or matrix that provides homogeneous and precisely regulated energy delivery with low thermal spread. The PTC conductive-resistive matrix can be a variably resistive body that comprises a polypropylene or a medical grade silicone polymer that is doped with conductive particles (e.g., carbon). Polymer PTC materials are known in the field of over current protection devices that will "trip" and become resistant when a selected trip current is exceeded. Although in the illustrated embodiment the electrode 56 is a single electrode that is associated with the lower jaw 54, in other embodiments multiple electrodes can be used, and one or more electrodes can be disposed on either or both of the upper and lower jaws 52, 54.

Figure 8B:
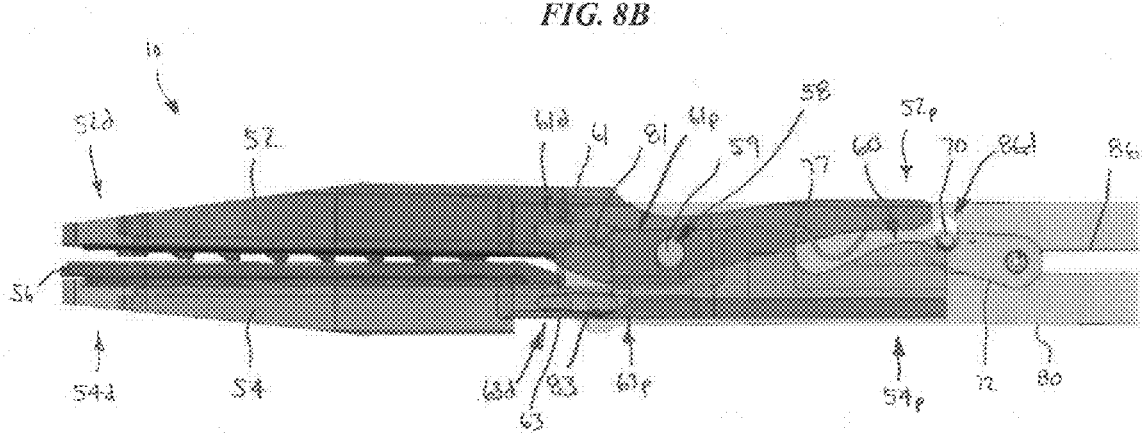
FIG. 8B is a partially transparent side view of the upper and lower jaws of FIG. 8A as they move towards a closed position, proximal ends of the upper and lower jaws forming a track that receives the pin of FIG. 7.
Figure 8C:
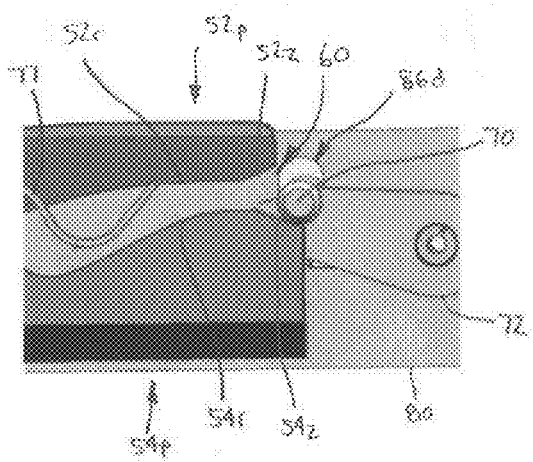
FIG. 8C is a detailed side view of the pin entering the track of FIG. 8B.

A person skilled in the art will appreciate that the second and first jaws 52, 54 can have any suitable shape and length for engaging tissue, with the shape, length, and overall configuration being selected, at least in part, based on the targeted anatomical structure for treatment and the other components with which the jaws 52, 54 are being used. As shown in FIGS. 3B and 4B, distal ends 52*d*, 54*d* of the upper and lower jaws 52, 54 can taper away from the respective longitudinal axes $L_2$, $L_3$ of the jaws. Opposed track portions 52*r* of the bottom surface 52*b* and opposed track portions 54*r* of the top surface 54*t* located at the proximal ends 52*p*, 54*p* of the jaws can have a curved configuration that form the track or path 60 through which the biasing member, e.g., the cantilever beam or pin 70, can pass when the jaws 52, 54 are in the closed position (FIGS. 2 and 8B). Chamfers 52*z*, 54*z* can be formed at track entry points of the respective jaws 52, 54 to help receive the pin 70 in the track 60. A remainder of the shape of the track 60 formed by the track portions 52*r*, 54*r* can be configured to provide desired positions for the pin 70 during the course of operating the device 10. For example, a position at which the pin 70 applies a spring bias to the upper jaw 52, referred to herein as a compressive load application position, can be at a narrowest point 60*n* of the track 60 (FIGS. 2 and 8E). The curves of the track portions 52*r*, 54*r* disposed distal of the narrowest point 60*n* can form in a resting position for the pin 70 in which the lower jaw track portion 54*r* is configured to have the pin 70 remain in contact with it while the upper jaw track portion 52*r* is spaced a distance apart from the lower jaw track portion 54*r*. As a result, the upper jaw track portion 52*r* does not generally contact the pin 70 at this more distal location that is the resting position.

Opposed second paths or tracks 66 can be formed in opposed inner surfaces 54*i* of the lower jaw 54. These tracks 66 provide an alternate return path through which the pin 70 can travel when moving from the resting position back to an initial position. As described in greater detail below, by providing an alternate route for the pin 70 to travel, the compressive force applied at the compressive load application position can be avoided when returning the pin 70, and thus the cutting blade assembly 80 associated therewith, back to the initial position.

Other features can be incorporated into the end effector 50. By way of non-limiting example, features for measuring or otherwise determining an amount of force and/or compression applied to the tissue by the jaws 52, 54 can be incorporated into the device 10. Likewise, components configured to notify an operator when certain threshold values, e.g., loads, are attained can be provided, whether such notification is visual, audible, or in some other form. A person skilled in the art will understand exemplary components having these features and will also understand how to integrate such components with the present disclosures. Additionally, any type of material known to those skilled in the art can be used to manufacture the components of the end effector 50, the shaft 40, and the handle portion 20. In some exemplar embodiments, the jaws 52, 54 and shaft 40 are made from surgical grade stainless steel (e.g., 17-4), the housing 22 of the handle portion is made from a polymer (e.g., polycarbonate), and components disposed in the handle portion, e.g., motors, controllers, levers, are made from various materials typically used to form such components.

Figure 5A:
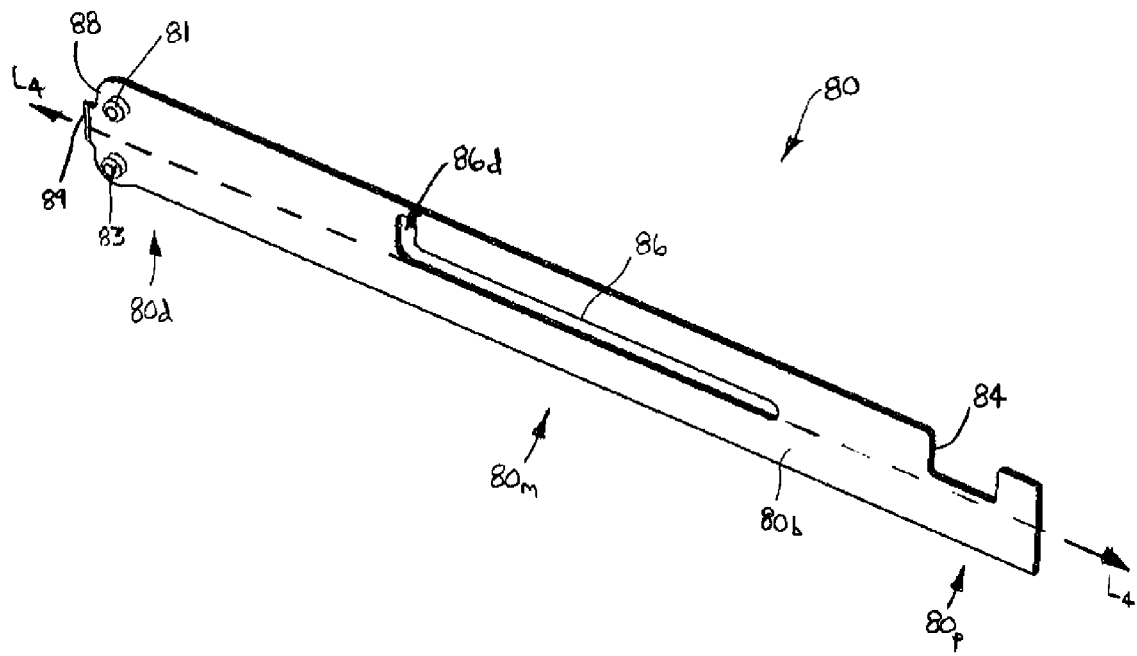
FIG. 5A is a side perspective view of the cutting blade assembly of FIG. 2.
Figure 5B:
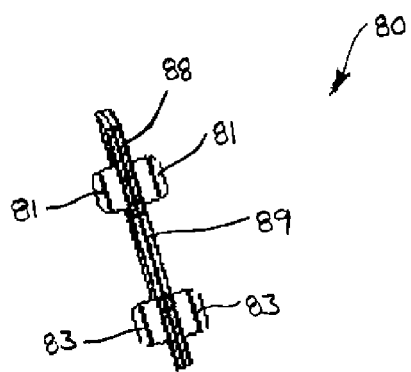
FIG. 5B is a front perspective view of the cutting blade assembly of FIG. 5A.

FIGS. 5A and 5B illustrates one embodiment of a cutting blade assembly 80, sometimes referred to as a knife or blade by those skilled in the art, among other names, which can be used in conjunction with the handle portion 20, shaft 40, and end effector 50. In the illustrated embodiment, the cutting blade assembly 80 also supplies a compressive force to the jaws 52, 54 to cause them to close, as described in greater detail below. Thus, the cutting blade assembly 80 can alternately be referred to as a compression member.

The cutting blade assembly 80 can have various sizes, shapes, and configurations, as will be appreciated by a person skilled in the art. In general, the cutting blade assembly 80 can have at least one elongate drive beam 80*b*, also referred to as a pusher shaft, which is its body, and which can be longitudinally movable along a length of the jaws 52, 54. In the illustrated embodiment, there are actually three drive beams disposed aligned and adjacent to each other, although any number of drive beams, including a single drive beam, can be used. Each drive beam 80*b* can have a proximal end 80*p*, a distal end 80*d*, and a medial portion 80*m* extending between the proximal and distal ends. The proximal end 80*p* and the medial portion 80*m* can be sized and shaped to reciprocate within the bore 42 of the elongate shaft 40, with the proximal end 80*p* also being configured to mate with actuating components of the handle portion 20, such as a lever arm. As shown, the proximal end 80*p* includes a cut-out portion 84 that is complementary to mating features of the actuating components of the handle portion 20.

The medial portion 80*m* includes an elongate slot 86 extending through the vertically-extending body 80*b* and extending a length of the medial portion 80*m* in a proximal-distal direction. The elongate slot 86 can be configured to receive the biasing member, e.g., the cantilever beam or pin 70 (FIGS. 6 and 7), such that the pin 70 can slide through a length of the slot 86. As shown, a distal end 86*d* of the slot 86, also referred to as a second portion of the slot 86, can have a diameter that is substantially larger than a diameter of the pin 70, and substantially larger than a diameter of the rest of the slot 86, to provide tolerance as the pin 70 enters the track 60, i.e., the pin 70 can float in the distal end 86*d* to help it enter the track 60. The second portion of the slot 86 can be described as being substantially perpendicular to the rest of the slot 86. Further, as illustrated (e.g., FIG. 8B) the slot 86 can be located below or approximately in-line with the track portion 54*r* of the lower jaw 54 so that the pin 70 can ride the track portion 54*r* as it enters and travels through the track 60.

The distal end 80*d* of the cutting blade assembly 80 can be sized and shaped to interact with the jaws 52, 54, for instance by being slidably coupled to the jaws. A central longitudinal axis $L_4$ of the cutting blade assembly 80 can be aligned and coaxial with the central longitudinal axis shaft $L_1$ of the shaft 40, and can be substantially parallel to the longitudinal axes $L_2$, $L_3$ of the upper and lower jaws 52, 54, although other configurations are possible. Further, as shown, the cutting blade assembly 80 can include first and second guides 81, 83 that form an "I-beam" configuration to assist in applying a compressive force to the jaws 52, 54. The configuration is referred to as an "I-beam" configuration because, as shown in FIG. 5B, a cross-sectional shape of the cutting blade assembly 80 looks similar to an "I-beam." The first and second guides 81, 83 can extend in both directions substantially perpendicular to a main surface of the drive beams 80*b*. The guides 81, 83 can be complementary in shape to the slots 61, 63 formed in the jaws 52, 54 such that the guides 81, 83 can travel distally through the slots 61, 63, and in doing so, can apply a compressive force to the jaws 52, 54. In the illustrated embodiment the guides 81, 83 have a tubular shape, although any other number of shapes, such as substantially flat and/or substantially rectangular flanges, can be used, depending, at least in part, on the configuration of the slots 61, 63 and other components of the device 10. Sliding contact of the lateral edges of the guides 81, 83 and sides of the slots 61, 63 can prevent lateral flexing of the jaws 52, 54. In some embodiments, the cutting blade 89 can be recessed relative to the guides 81, 83 so that compression occurs prior to transecting or cutting of the tissue.

A vertical strut 88 of the drive beam body can have a blade or knife edge 89 formed on or otherwise attached thereto. In the illustrated embodiment, the knife edge 89 extends from the outermost drive beams 80b to encompass each of the three drive beams 80b. As will be appreciated by a person skilled in the art, in other embodiments the knife edge 89 may be detached from the cutting blade assembly 80 such that the cutting blade assembly 80 is only used as a compression member and the knife edge 89 is advanced and retracted as its own, separate cutting mechanism. In still other embodiments, the knife edge 89 can include a transverse electrode, or alternatively, the vertical strut 88 can include a transverse electrode, with the transverse electrode in either instance being configured to assist in cutting or transecting tissue. In instances in which the vertical strut 88 includes a transverse electrode, a separate knife edge or blade can be eliminated.

Figure 7:
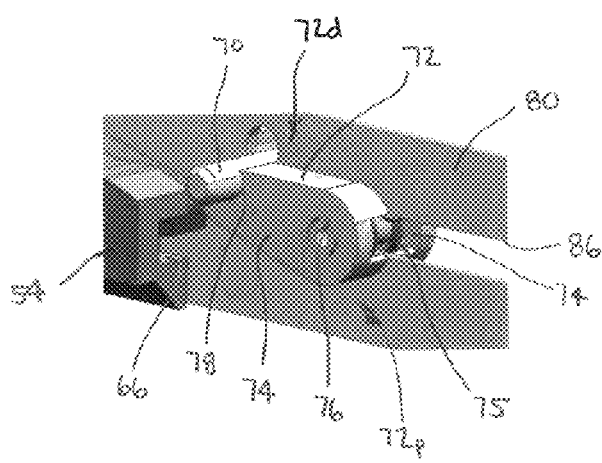
FIG. 7 is a detailed perspective view of a lever and a pin configured to apply a compressive force to the upper jaw of FIG. 6.

A biasing member or element is illustrated in FIGS. 6 and 7 and can include a cantilever beam or pin 70 configured to be disposed in the elongate slot 86 of the cutting blade assembly 80. The biasing member can also include a spring-loaded lever 72 configured to bias the pin 70 into the slot 86. The pin 70 can be any size, shape, and material, depending at least in part on the other components with which it is used. As shown the pin 70 is substantially cylindrical, has a length that is longer than a width of the cutting blade assembly 80 and long enough to extend into both second paths 66 of the lower jaw 54, and is made of a metal, such as a surgical grade stainless steel. The lever 72 can likewise have any size and shape, and be made of any material, including a surgical grade stainless steel or polymer. As shown, the lever 72 has opposing bodies 74 on opposite sides of the cutting blade assembly 80. A proximal end 72p of the lever 72 can be coupled to the cutting blade assembly 80 by way of a pin 76 extending between the two bodies 74 and through the slot 86 of the cutting blade assembly 80. A distal end 72d of the lever 72 can have a ledge 78 for engaging the pin 70. The lever 72 can also include a torsion spring 75 disposed therein and configured to bias the pin 70 into the slot 86.

In some embodiments, one or more leaf springs 77 can be included to assist in maintaining a desired location of the pin 70 with respect to the cutting blade assembly 80 and jaws 52, 54. As shown, opposed leaf springs 77 (only one is illustrated) can be attached to the top surface 54t of the lower jaw 54. In particular, after the pin 70 passes from the compressive load application position to a resting position, the leaf springs 77 can be configured to engage the pin 70 and bias it in a downward direction B, towards the lower jaw 54, to maintain the pin 70 in the resting position. As a result, as the cutting blade assembly 80 continues to distally advance, the leaf springs 77 engage the pin 70 and prevent the pin from also distally advancing. In such a configuration, the pin 70 moves relative to the slot by virtue of the slot 86 advancing distally while the pin 70 is held substantially in place by the leaf springs 77.

Furthermore, when the cutting blade assembly 80 is retracted, the downward force supplied by the leaf springs 77, in conjunction with a force supplied to the pin 70 by the distal end 86d of the slot 86 during a return stroke, can push the pin 70 into the second path 66. The pin can then travel the length of the second path 66, and upon exiting the path 66, be biased back into the slot 86 by the lever 72 to return the pin 70 to its initial position. A person skilled in the art will recognize that reference to an initial position, and to any other position described herein, e.g., a compressive load application position and a resting position, does not define a single location, but rather a range of locations during which a particular result is achieved. For example, in an initial position, illustrated for example in FIG. 6, the pin 70 can be at any location that is proximal of the position at which the spring bias is supplied to the upper jaw 52 by the pin 70, i.e., the compressive load application position, and still be considered in the initial position. Likewise, a resting position can be any location at which the pin is distal of the compressive load application position such that it is not supply a spring bias to the jaws 52, 54.

FIGS. 8A-8J illustrate one exemplary embodiment of the device 10 in use. As shown in FIG. 8A, the jaws 52, 54 are in an open position with the proximal end 52p of the upper jaw 52 being disposed in the opening 54o of the lower jaw 54 and the distal ends 52d, 54d being spaced a distance apart so that tissue to be grasped and sealed can be disposed therebetween. The guides 81, 83 of the cutting blade assembly 80 can be disposed in the proximal ends 61p, 63p of the jaw slots 61, 63 with the cutting blade assembly 80 being located at a proximal-most position and ready to perform a first stroke to close the jaws 52, 54. The pin 70 can be located in the distal end 86d of the slot 86, and can float therein due to the larger diameter of the distal end 86d in comparison to the diameter of the pin 70.

A first stroke can be fired by the actuating lever 24 (not shown), thereby causing the cutting blade assembly 80 to advance distally. This movement can cause the guides 81, 83 to slide within the first slots 61, 63, and because the first slot 63 is ramped, a compressive force is imparted on the upper jaw 52 to advance it towards the closed position, as shown in FIG. 8B. As the jaws 52, 54 advance towards the closed position, the proximal end 52p of the upper jaw 52 swings away from the proximal end 54p of the lower jaw 54, and the track 60 for receiving the pin 70 is formed. As shown in FIG. 8C, the pin 70 can begin to enter the track 60 as the cutting blade assembly 80 advances distally, going from a floating position within the distal end 86d of the slot 86 to engaging and riding along the top surface 54t of the lower jaw track portion 54r. By allowing the pin 70 to float in the slot 86, and by including features such as chamfers 52z, 54z at the entry point of the track 60, the tolerances for the system can be more manageable than in existing systems, which often require very tight tolerances.

Figure 8D:
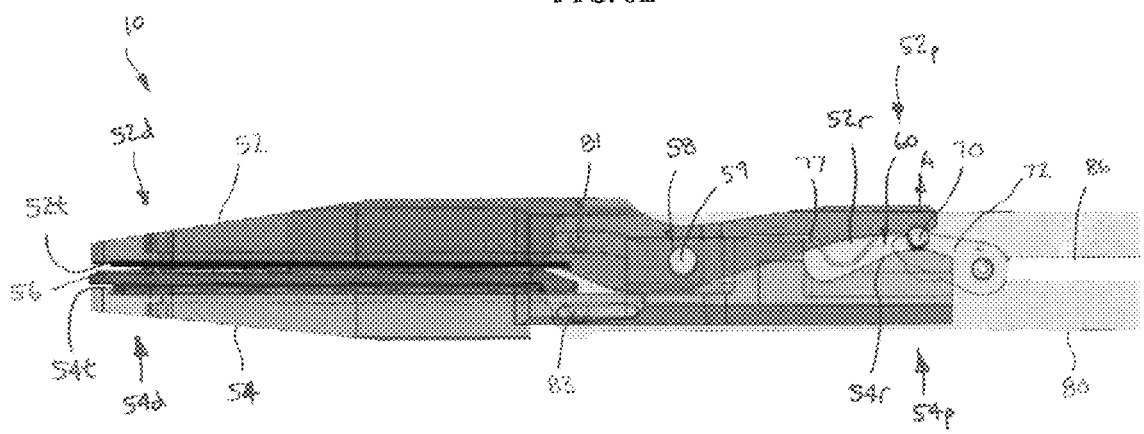
FIG. 8D is a partially transparent side view of the upper and lower jaws of FIG. 8B in the closed position with the pin being in a compressive load application position.
Figure 8E:
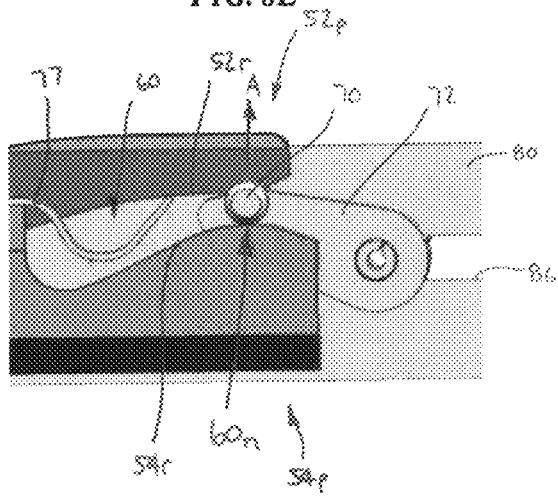
FIG. 8E is a detailed side view of the pin being disposed in the compressive load application position of FIG. 8D.

As the first stroke comes to completion, the jaws 52, 54 can move to a fully closed position in which the facing surfaces 52b, 54t thereof grasp a tissue extending therebetween, illustrated in FIG. 8D. In particular, the electrode 56 coupled to the top surface 54t of the lower jaw 54 engages tissue in conjunction with the bottom surface 52b of the upper jaw 52. The pin 70 can continue to ride along the lower jaw track surface 54r. As shown in FIG. 8E, as the pin 70 advances distally, it eventually also abuts, or otherwise engages, the upper jaw track portion 52r. In this location, the pin 70 is now in the compressive load application position. More specifically, at or near the narrowest point 60n of the track 60 the pin 70 engages both the upper and lower track portions 52r, 54r and acts as a spring bias by applying a force to the proximal end 52p of the upper jaw 52 in a direction A. This causes the upper jaw 52 to pivot around the pivot point 58 in a counter clockwise direction such that a compressive force is applied towards the lower jaw 54. The result can be a substantially steady compressive force that is applied to the tissue engaged by the jaws 52, 54. More particularly, the load applied to the jaws 52, 54 due to the pin 70 engaging the upper and lower track portions 52r, 54r can be greater than the load applied to the jaws 52, 54 by only the guides 81, 83 of the cutting blade assembly 80. Accordingly, the load applied to the tissue engaged by the jaws 52, 54 when the pin 70 engages the upper and lower portions 52r, 54r can also be greater than the load applied to the tissue when the jaws 81, 83 are closed but before the pin 70 engages the upper and lower track portions 52r, 54r. In some instances, the compressive load application position can also be referred to as a pre-cut position because the application of the compressive force by the biasing member can occur prior to performing any meaningful or substantial cutting or transecting of the tissue disposed between the jaws 52, 54.

Further, while the pin 70 is in the compressive load application position, the button 28 (not shown) of the handle portion 20 can be operated to supply electrical energy to the electrode 56, and thus to the tissue grasped by the jaws 52, 54. The electrical energy can help weld or otherwise seal the tissue. In earlier embodiments of devices that seal and transect, often the compressive force supplied to the tissue by the jaws 52, 54 decreased as the tissue was sealed. The spring bias supplied by the pin 70, track 60, and related components of the present disclosure, however, help maintain a substantially steady compressive force and/or increase the amount of compressive force supplied to the tissue by the jaws 52, 54. Additionally, this substantially steady or increased compressive force can help reduce a load on the cutting blade assembly 80, and can enable higher forces for grasping the tissue that could not be achieved using previous tissue grasping and sealing devices.

After the tissue has been sealed and/or the compressive force resulting from the spring bias-supplying mechanism is no longer desired, a second stroke can be fired by the actuating lever 24 to transect the sealed tissue. In some configurations, features such as gauges and signals can be incorporated into the device 10 to let the operator know that sealing is completed and that transection can commence. Firing the second stroke can again cause the cutting blade assembly 80 to advance distally. As shown, the guides 81, 83 can advance out of the first slots 61, 63 and can slidably engage a surface 52s, 54s of the jaws 52, 54 located distal of the slots 61, 63. In other embodiments the slots 61, 63 can extend further distally, providing a path for the guides 81, 83 for the entirety of the second stroke as well.

Figure 8F:
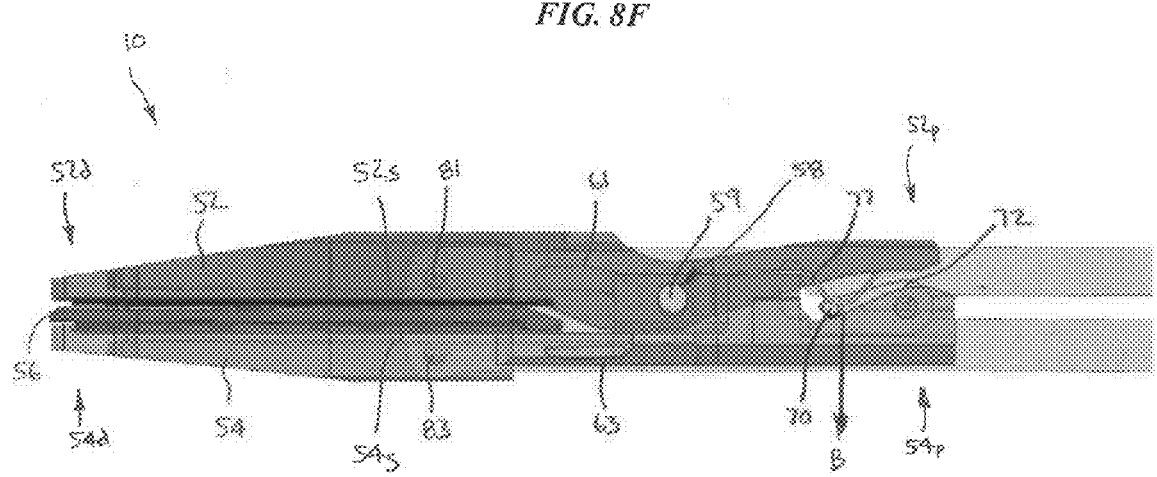
FIG. 8F is a partially transparent side view of the upper and lower jaws of FIG. 8D in the closed position with the pin being in a resting position and the cutting mechanism being advanced through a portion of the upper and lower jaws.
Figure 8G:
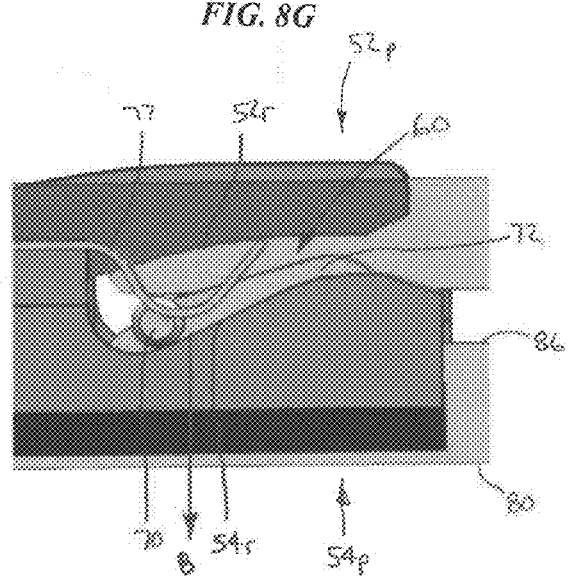
FIG. 8G is a detailed side view of the pin being disposed in the resting position of FIG. 8F.

While the cutting blade assembly 80 continues to advance distally during the second stroke, as shown in FIGS. 8F and 8G, the pin 70 does not continue distal advancement for the entirety of the second stroke. The pin 70 first falls out of engagement with the upper track portion 52r such that the additional compressive force in the direction A is no longer supplied by the pin 70. However, the compressive force supplied by the guides 81, 83 of the cutting blade assembly 80 can continue to supply compressive force to the jaws 52, 54 such that the tissue disposed between the jaws can continue to be grasped. As the pin 70 slides along the lower jaw track portion 54r, it can eventually be engaged by the leaf springs 57 and prevented from advancing further distally by a downward force B supplied by the leaf springs 57. The pin 70 can be held substantially in place against the lower jaw track portion 54r by the leaf springs 57 and the slot 86 in which the pin 70 is disposed can slide over the pin to advance distally with the rest of the cutting blade assembly 80.

Figure 8H:
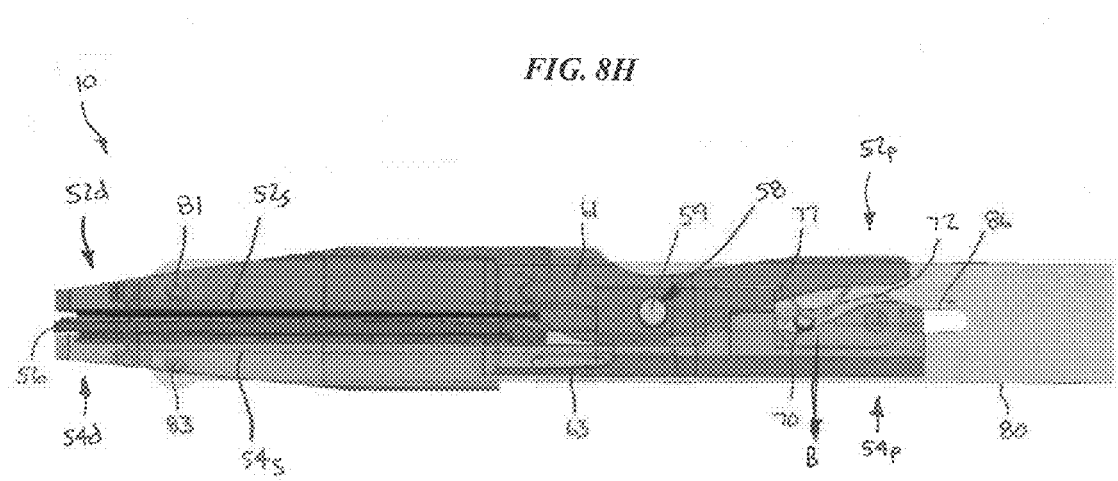
FIG. 8H is a partially transparent side view of the upper and lower jaws of FIG. 8F in the closed position with the pin in a resting position and the cutting mechanism being advanced further distally through the upper and lower jaws than in FIG. 8F.

As shown in FIG. 8H, the cutting blade assembly 80 can pass through a length of the jaws 52, 54 to their distal ends 52d, 54d to complete the cutting stroke of the cutting blade assembly 80. As the cutting stoke continues, the pin 70 remains engaged by the leaf springs 57 in the resting position. The cutting blade assembly 80 can then be retracted proximally, either as part of the second stroke, or by other mechanisms disclosed above or known to those skilled in the art.

Figure 8I:
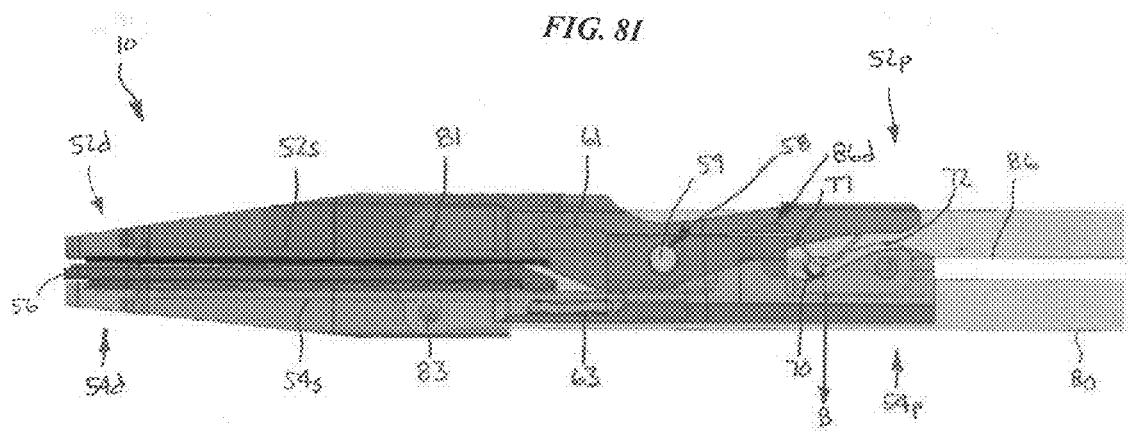
FIG. 8I is a partially transparent side view of the upper and lower jaws of FIG. 8H in the closed position with the pin in a resting position and the cutting mechanism being proximally retracted with respect to the upper and lower jaws.
Figure 8J:
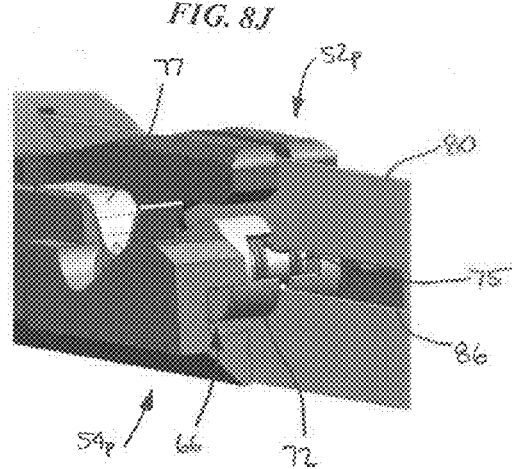
FIG. 8J is a detailed perspective view of a lower portion of a track formed in the lower jaw of FIG. 8 through which the pin travels as the cutting mechanism is proximally retracted.

FIG. 8I illustrates the cutting blade assembly 80 as it begins to retract. During the first stages of retraction, the pin 70 remains substantially in place due to its engagement with the leaf springs 57. However, the distal end 86d of the slot 86 can engage the pin 70 as it retracts, and the axial force supplied by the distal end 86d of the slot 86 in combination with the downward force B supplied by the leaf springs 57 can direct the pin 70 downward into the second path 66, as illustrated in FIG. 8J. By passing the pin 70 through the second track 66, rather than having it retrace the path it took through the first path 60, an increased compressive force is not applied to the treated tissue. This can be advantageous because it decreases the risk of damaging the treated tissue. Once the pin 70 exits the second path 66, it can be biased back into the slot 86 by the lever 72 having the torsion spring 75, and return to its initial position for subsequent use.

A person skilled in the art will appreciate that the present invention has application in conventional endoscopic and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a jaw assembly having a first jaw and a second jaw pivotally coupled thereto, the first and second jaws being configured to engage tissue therebetween;
   a cutting blade assembly slidably coupled to the first and second jaws and configured such that distal advancement of the cutting blade assembly along the first and second jaws moves the second jaw toward the first jaw into a closed position, and proximal retraction of the cutting blade assembly along the first and second jaws allows the second jaw to pivot away from the first jaw into an open position; and
   a biasing member coupled to the cutting blade assembly, the biasing member being configured to advance distally along a track to apply a compressive force to the second jaw during initial distal advancement of the cutting blade assembly along a proximal portion of the first and second jaws, and the biasing member further being configured to apply no compressive force to the second jaw during further distal advancement of the cutting blade assembly along a distal portion of the first and second jaws,
   wherein a size of the track is configured to change as the first and second jaws move towards the closed position, and
   wherein a width of the pin path is smaller at a point at which the biasing member applies the compressive force to the second jaw than a width of the pin path at a point at which the biasing member applies no compressive force to the second jaw when the jaws are in the closed position.

2. The device of claim 1, wherein the biasing member is configured to travel along a first path during distal advancement of the cutting blade assembly, and is configured to travel along a second alternate path during proximal retraction of the cutting blade assembly.

3. The device of claim 2, further comprising a leaf spring coupled to the first jaw and configured to bias the biasing member into the second alternate path during proximal retraction of the cutting blade assembly.

4. The device of claim 1, wherein the second jaw is pivotally coupled to the first jaw at a pivot point that is located distal of the proximal portion of the first and second jaws along which the compressive force is applied.

5. The device of claim 1, wherein the biasing member comprises a pin configured to abut a proximal end of the second jaw to bias the second jaw toward the closed position during initial distal advancement of the cutting blade assembly.

6. The device of claim 5, further comprising a leaf spring coupled to the first jaw and configured to bias the pin away from the proximal end of the second jaw during further distal advancement of the cutting blade assembly along a distal portion of the first and second jaws.

7. The device of claim 5, wherein the cutting blade assembly includes a pusher shaft having a slot formed therein, and wherein the pin is slidably disposed within the slot.

8. The device of claim 7, wherein the slot includes a first portion extending in a proximal-distal direction, and a second portion extending substantially perpendicular to the first portion.

9. The device of claim 1, further comprising an electrode coupled to at least one of the first and second jaws and configured to apply energy to tissue disposed between the first and second jaws.

10. The device of claim 1, wherein the track is defined by a proximal portion of an uppermost surface of the first jaw and a proximal portion of a lowermost surface of the second jaw.

11. A surgical device, comprising:
    an elongate shaft having an end effector with opposed jaws on a distal end thereof; and
    an actuation assembly coupled to the opposed jaws and configured to advance distally along the opposed jaws to close the jaws, and to retract proximally along the jaws to allow the jaws to open, the actuation assembly having a pin coupled thereto and configured to travel along a first pin path during distal advancement of the actuation assembly, and to travel along a second alternative pin path during proximal retraction of the actuation assembly, wherein the first pin path is configured such that the pin applies an increased compressive force to the opposed jaws during at least a portion of travel along the first pin path, and wherein the first pin path is further configured such that the pin applies no compressive force to the opposed jaws during travel along the second alternative pin path,
    wherein a surface along which the pin is configured to travel when traveling along the first pin path during distal advancement of the actuation assembly is a different surface then a surface along which the pin is configured to travel when traveling along the second alternative pin path during proximal retraction of the actuation assembly, and
    wherein the first pin path includes a total distance that the pin travels during distal advancement of the actuation assembly.

12. The device of claim 11, further comprising a spring configured to bias the pin into the second alternative pin path during proximal retraction of the actuation assembly.

13. The device of claim 11, wherein the actuation assembly includes a cutting blade configured to cut tissue engaged between the opposed jaws.

14. The device of claim 11, wherein the opposed jaws comprises a cartridge assembly and an anvil pivotally coupled to one another at a pivot point.

15. The device of claim 14, wherein the first pin path is configured such that the pin applies the increased compressive force to the opposed jaws during a portion of travel along the first pin path located proximal to the pivot point.

16. The device of claim 11, wherein the first pin path has a width that is larger at a distal end of the first pin path than at an intermediate portion of the first pin path, the intermediate portion being located at a location at which the first pin path is configured such that the pin applies the increased compressive force to the opposed jaws.

17. The device of claim 11, wherein the first pin path is configured such that the pin applies a force to a first wall and a second wall of the first pin path simultaneously during at least a portion of travel along the first pin path.

18. The device of claim 11, wherein the actuation assembly is configured such that the pin advances distally to apply a compressive force to a jaw of the opposed jaws during the first distal advancement step.

19. The device of claim 11,
    wherein the first pin path is defined by a proximal portion of an uppermost surface of a first jaw of the opposed jaws and a proximal portion of a lowermost surface of a second jaw of the opposed jaws.

20. The device of claim 19, wherein the second alternative pin path is disposed in one of the opposed jaws.

21. The device of claim 11, wherein the surface along which the pin is configured to travel when traveling along the first pin path during distal advancement of the actuation assembly is disposed above the surface along which the pin is configured to travel when traveling along the second alternative pin path.

22. The device of claim 11,
wherein the first pin path has first and second terminal ends,
wherein the second alternative pin path has first and second terminal ends, and
wherein the first terminal end of the first pin path is neither the first nor second terminal end of the second alternative pin path.

23. A method for sealing tissue, comprising:
distally advancing a cutting assembly of a surgical access device to apply a first compressive force to at least one of a first jaw and a second jaw of the device to move the jaws into a closed position in which tissue is clamped by the jaws, the device having a biasing element coupled to the cutting assembly that travels along a pin path to apply a second compressive force to the second jaw when the jaws are in the closed position; and
further distally advancing the cutting assembly along the first and second jaws such that the biasing element no longer applies the second compressive force to the second jaw,
wherein a size of the pin path changes as the first and second jaws move towards the closed position, and
wherein a width of the pin path is smaller at a point at which the biasing element applies the second compressive force to the second jaw than a width of the pin path at a point at which the biasing element no longer applies the second compressive force to the second jaw when the jaws are in the closed position.

24. The method of claim 23, further comprising delivering energy to the tissue through at least one of the first and second jaws prior to the step of further distally advancing the cutting assembly along the first and second jaws such that the biasing element no longer applies the second compressive force to the second jaw.

25. The method of claim 23, wherein the biasing element travels along the pin path, which is formed between the first and second jaws, and the biasing element applies the second compressive force to a proximal end of the second jaw.

26. The method of claim 25, further comprising:
proximally retracting the cutting assembly, the biasing element traveling along an alternate path during proximal movement of the cutting assembly such that the biasing element applies no compressive force to the second jaw,
wherein a surface along which the biasing element travels when traveling along the pin path during distal advancement of the cutting assembly is a different surface then a surface along which the biasing element travels along the alternate pin path during proximal movement of the cutting assembly, and
wherein the pin path includes a total distance that the biasing element travels during distal advancement of the cutting assembly.

27. The method of claim 26, wherein the alternate path is disposed in one of the first and second jaws.

28. The method of claim 25, wherein the pin path is defined by a proximal portion of an uppermost surface of the first jaw and a proximal portion of a lowermost surface of the second jaw.

29. The method of claim 23, wherein further distally advancing the cutting assembly along the first and second jaws includes transecting the tissue disposed between the jaws.

30. A surgical device, comprising:
a jaw assembly having a first jaw and a second jaw pivotally coupled thereto, the first and second jaws being configured to engage tissue therebetween;
a cutting blade assembly slidably coupled to the first and second jaws and configured such that distal advancement of the cutting blade assembly along the first and second jaws moves the second jaw toward the first jaw into a closed position, and proximal retraction of the cutting blade assembly along the first and second jaws allows the second jaw to pivot away from the first jaw into an open position; and
a biasing member coupled to the cutting blade assembly, the biasing member being configured to advance distally along a track to apply a compressive force to the second jaw during initial distal advancement of the cutting blade assembly along a proximal portion of the first and second jaws, and the biasing member further being configured to apply no compressive force to the second jaw during further distal advancement of the cutting blade assembly along a distal portion of the first and second jaws,
wherein the track is defined by a proximal portion of an uppermost surface of the first jaw and a proximal portion of a lowermost surface of the second jaw, and
wherein a size of the track is configured to change as the first and second jaws move towards the closed position.

31. The surgical device of claim 30, wherein the biasing member is configured to travel along a first path during distal advancement of the cutting blade assembly, and is configured to travel along a second alternate path during proximal retraction of the cutting blade assembly.

32. The surgical device of claim 31, further comprising a leaf spring coupled to the first jaw and configured to bias the biasing member into the second alternate path during proximal retraction of the cutting blade assembly.

33. The surgical device of claim 30, wherein the second jaw is pivotally coupled to the first jaw at a pivot point that is located distal of the proximal portion of the first and second jaws along which the compressive force is applied.

34. The surgical device of claim 30, wherein the biasing member comprises a pin configured to abut a proximal end of the second jaw to bias the second jaw toward the closed position during initial distal advancement of the cutting blade assembly.

35. The surgical device of claim 30, further comprising an electrode coupled to at least one of the first and second jaws and configured to apply energy to tissue disposed between the first and second jaws.

36. A method for sealing tissue, comprising:
distally advancing a cutting assembly of a surgical access device to apply a first compressive force to at least one of a first jaw and a second jaw of the device to move the jaws into a closed position in which tissue is clamped by the jaws, the device having a biasing element coupled to the cutting assembly that travels along a pin path to apply a second compressive force to the second jaw when the jaws are in the closed position;
further distally advancing the cutting assembly along the first and second jaws such that the biasing element no longer applies the second compressive force to the second jaw; and proximally retracting the cutting assembly, the biasing element traveling along an alternate path during proximal movement of the cutting assembly such that the biasing element applies no compressive force to the second jaw, wherein a size of the pin path changes as the first and second jaws move towards the closed position, wherein the biasing element travels along the pin path, which is formed between the first and second jaws, and the biasing element applies the second compressive force to a proximal end of the second jaw, wherein a surface along which the biasing element travels when traveling along the pin path during distal advancement of the cutting assembly is a different surface then a surface along which the biasing element travels along the alternate pin path during proximal movement of the cutting assembly, and wherein the pin path includes a total distance that the biasing element travels during distal advancement of the cutting assembly.

37. The method of claim 36, further comprising delivering energy to the tissue through at least one of the first and second jaws prior to the step of further distally advancing the cutting assembly along the first and second jaws such that the biasing element no longer applies the second compressive force to the second jaw.

38. The method of claim 36, wherein further distally advancing the cutting assembly along the first and second jaws includes transecting the tissue disposed between the jaws.

39. The method of claim 36, wherein the pin path is defined by a proximal portion of an uppermost surface of the first jaw and a proximal portion of a lowermost surface of the second jaw.

* * * * *